(12) United States Patent
Yi et al.

(10) Patent No.: US 8,953,741 B2
(45) Date of Patent: Feb. 10, 2015

(54) SYSTEM AND METHOD FOR MEASURING ASH CONTENT AND CALORIFIED VALUE OF COAL

(71) Applicant: Tsinghua University, Beijing (CN)

(72) Inventors: Hongchang Yi, Beijing (CN); Lin Qian, Beijing (CN)

(73) Assignee: Tsinghua University (CN)

( * ) Notice: Subject to any disclaimer, the term of this patent is extended or adjusted under 35 U.S.C. 154(b) by 286 days.

(21) Appl. No.: 13/656,177

(22) Filed: Oct. 19, 2012

(65) Prior Publication Data

US 2013/0101087 A1   Apr. 25, 2013

(30) Foreign Application Priority Data

Oct. 19, 2011  (CN) .......................... 2011 1 0319408

(51) Int. Cl.
*G01N 23/087* (2006.01)
*G01N 23/12* (2006.01)
*G01N 23/14* (2006.01)
*G01N 23/083* (2006.01)
*G01N 33/22* (2006.01)

(52) U.S. Cl.
CPC ............ *G01N 23/083* (2013.01); *G01N 33/222* (2013.01); *G01N 2223/617* (2013.01); *G01N 2223/643* (2013.01)
USPC ................... 378/53; 378/45; 378/57; 378/83; 378/88

(58) Field of Classification Search
USPC ..................... 378/45, 53, 57, 83, 88
See application file for complete search history.

(56) References Cited

U.S. PATENT DOCUMENTS 7,006,919 B2 * 2/2006 Osucha et al. ..................... 702/2
7,809,526 B1 * 10/2010 Lang .............................. 702/183

* cited by examiner

*Primary Examiner* — Robert Kim
*Assistant Examiner* — Hsien Tsai
(74) *Attorney, Agent, or Firm* — Lerner, David, Littenberg, Krumholz & Mentlik, LLP

(57) ABSTRACT

A system and a method for measuring an ash content and a calorific value of a coal are provided. The system comprises: at least two dual-energy gamma ray transmission measuring devices and a computing device, in which at least one first dual-energy gamma ray transmission measuring device is disposed before an inlet of a coal combustion apparatus for measuring a first attenuation coefficient of a gamma ray from the at least one first dual-energy gamma ray transmission measuring device with regard to the coal; at least one second dual-energy gamma ray transmission measuring device is disposed after an outlet of the coal combustion apparatus for measuring a second attenuation coefficient of a gamma ray from the at least one second dual-energy gamma ray transmission measuring device with regard to a coal ash; and the computing device is configured to compute the ash content and the calorific value of the coal.

13 Claims, 1 Drawing Sheet

US 8,953,741 B2

SYSTEM AND METHOD FOR MEASURING ASH CONTENT AND CALORIFIED VALUE OF COAL

CROSS REFERENCE TO RELATED APPLICATION

This application claims priority to and benefits of Chinese Patent Application No. 201110319408.1, filed with State Intellectual Property Office, P. R. C. on Oct. 19, 2011, the entire content of which is incorporated herein by reference.

FIELD

Embodiments of the present disclosure generally relate to a coal detection field, and more particularly, to a system and a method for measuring an ash content and a calorific value of a coal.

BACKGROUND

A dual-energy gamma ray transmission method is currently widely used for measuring an ash content of a coal. By measuring attenuation coefficients of gamma rays with two different levels of energy from a dual-energy gamma ray transmission measuring device with regard to a coal flow, the ash content of the coal is computed, and thus a calorific value of the coal may be derived from the ash content of the coal. This method is real-time, rapid, convenient to operate, and suitable for a coal utilization site which has a fixed coal source.

However, a disadvantage of the method lies in that a measuring result is greatly influenced by a change in a content of a high-atomic-number element in the coal. For example, the measuring result of the ash content is directly influenced by a change in a content of an element such as Fe or Ca in the coal. For a coal utilization site such as a thermal power plant, which has complicated coal sources, because the coal used comes from a plurality of mines or production regions, in general, the change in the content of the high-atomic-number element in the coal is larger, and thus an error will be larger when this method is used to measure the ash content of the coal. Moreover, it is difficult to solve the problem by calibration, because a calibrated parameter used for computing the ash content is accurate only for a coaly being calibrated, and once the coaly has varied, a larger error may be generated when the calibrated parameter is used to compute the ash content. However, in practice, a change in the coaly is usually irregular and difficult to predict, and therefore it is difficult to use this method for measuring the ash content in a case of complicated coal sources.

SUMMARY

Embodiments of the present disclosure seek to solve at least one of the problems existing in the prior art to at least some extent, or to provide a consumer with a useful commercial choice. Particularly, a system and a method for measuring an ash content and a calorific value of a coal are provided, which may not only meet requirements of real-time measurement, but also may eliminate an influence of a change in a content of a high-atomic-number element in the coal on a measurement of the ash content and the calorific value of the coal. Thus, the measurement may be more accurate and may not be influenced by the change in a coaly.

According to embodiments of a first broad aspect of the present disclosure, there is provided a system for measuring an ash content and a calorific value of a coal. The system comprises: at least two dual-energy gamma ray transmission measuring devices and a computing device, in which at least one first dual-energy gamma ray transmission measuring device is disposed before an inlet of a coal combustion apparatus for measuring a first attenuation coefficient of a gamma ray from the at least one first dual-energy gamma ray transmission measuring device with regard to the coal before combusted; at least one second dual-energy gamma ray transmission measuring device is disposed after an outlet of the coal combustion apparatus for measuring a second attenuation coefficient of a gamma ray from the at least one second dual-energy gamma ray transmission measuring device with regard to a coal ash formed by combusting the coal; and the at least two dual-energy gamma ray transmission measuring devices are connected with the computing device respectively to transmit the first attenuation coefficient and the second attenuation coefficient to the computing device, and the computing device is configured to compute the ash content and/or the calorific value of the coal based on the first attenuation coefficient and the second attenuation coefficient.

The first attenuation coefficient is influenced by contents of both a combustible element and a mineral element in the coal, the second attenuation coefficient is influenced only by an oxide of the mineral element, the change in the content of the high-atomic-number element (such as Fe or Ca) in the coal may influence both the first attenuation coefficient and the second attenuation coefficient, and a change in the ash content of the coal may only influence the first attenuation coefficient. Therefore, a part of the first attenuation coefficient influenced by the change in the content of the high-atomic-number element may be deducted by using the second attenuation coefficient, and thus the ash content and/or the calorific value of the coal may be computed accurately.

In one embodiment of the present disclosure, the at least two dual-energy gamma ray transmission measuring devices are connected with the computing device respectively via a cable or a wireless communication.

In one embodiment of the present disclosure, the at least one first dual-energy gamma ray transmission measuring device is disposed on a first transmission band connected with the inlet of the coal combustion apparatus.

In one embodiment of the present disclosure, the at least one second dual-energy gamma ray transmission measuring device is disposed on a second transmission band connected with the outlet of the coal combustion apparatus.

In one embodiment of the present disclosure, the at least one second dual-energy gamma ray transmission measuring device is disposed on a coal ash sampling apparatus near the outlet of the coal combustion apparatus for measuring the second attenuation coefficient of the coal ash output by the coal combustion apparatus and sampled by the coal ash sampling apparatus.

In one embodiment of the present disclosure, a correction delay time of the system is set based on a system running time for which the coal is transmitted from a first position where the first attenuation coefficient is measured to a second position where the second attenuation coefficient is measured, and the ash content and the calorific value of the coal are computed by the computing device based on the second attenuation coefficient measured at a current time and the first attenuation coefficient measured at a time which is one correction delay time forward from the current time. By setting the correction delay time of the system, it is ensured that the first attenuation coefficient and the second attenuation coefficient are measured for the same coal. Because the part of the first attenuation coefficient influenced by the change in the content of the high-atomic-number element is deducted by using the second attenuation coefficient, the ash content and/or the calorific value of the coal may be computed accurately.

In one embodiment of the present disclosure, the ash content and the calorific value of the coal are computed by the computing device based on the first attenuation coefficient measured at the current time and an average of a plurality of second attenuation coefficients measured in a fixed period of time forward from the current time. The fixed period of time may be adjusted according to various applications. Because a probability of a larger change in the coaly is slight within a short time interval, the average of the plurality of second attenuation coefficients may represent an actual second attenuation coefficient within a future short time. Furthermore, an error of the second attenuation coefficient by averaging is smaller, which is favorable for the measurement.

According to embodiments of a second broad aspect of the present disclosure, there is provided a method for measuring an ash content and a calorific value of a coal. The method comprises steps of: S01: before the coal is input into an inlet of a coal combustion apparatus, measuring a first attenuation coefficient of a gamma ray from at least one first dual-energy gamma ray transmission measuring device with regard to the coal before combusted; S02: after a coal ash formed by combusting the coal is output from an outlet of the coal combustion apparatus, measuring a second attenuation coefficient of a gamma ray from at least one second dual-energy gamma ray transmission measuring device with regard to the coal ash; S03: computing the ash content and the calorific value of the coal based on the first attenuation coefficient and the second attenuation coefficient.

In one embodiment of the present disclosure, a correction delay time is set based on a system running time for which the coal is transmitted from a first position where the first attenuation coefficient is measured to a second position where the second attenuation coefficient is measured, and the ash content and the calorific value of the coal are computed based on the second attenuation coefficient measured at a current time and the first attenuation coefficient measured at a time which is one correction delay time forward from the current time. By setting the correction delay time of the system, it is ensured that the first attenuation coefficient and the second attenuation coefficient are measured for the same coal. Because the part of the first attenuation coefficient influenced by the change in the content of the high-atomic-number element is deducted by using the second attenuation coefficient, the ash content and/or the calorific value of the coal may be computed accurately.

In one embodiment of the present disclosure, the ash content and the calorific value of the coal are computed based on the first attenuation coefficient measured at a current time and an average of a plurality of second attenuation coefficients measured in a fixed period of time forward from the current time, and thus a refined measuring result may be obtained. The fixed period of time may be adjusted according to various applications. Because a probability of a larger change in the coaly is slight within a short time interval, the average of the plurality of second attenuation coefficients may represent an actual second attenuation coefficient within a future short time. Furthermore, an error of the second attenuation coefficient by averaging is smaller, which is favorable for the measurement.

In one embodiment of the present disclosure, step S03 comprises steps of:

based on $$UL=[(1-x)*UmLC+x*UmLM]*pd \quad (1)$$

$$UH=[(1-x)*UmHC+x*UmHM]*pd \quad (2)$$

$$UmHC \approx UmHM \approx UH \quad (3)$$

where UL represents an attenuation coefficient of the first attenuation coefficient of a low-energy gamma ray of the gamma ray with regard to the coal, UH represents an attenuation coefficient of the first attenuation coefficient of a high-energy gamma ray of the gamma ray with regard to the coal, UmLC represents a mass attenuation coefficient of the low-energy gamma ray with regard to a combustible element in the coal, UmLM represents a mass attenuation coefficient of the low-energy gamma ray with regard to a mineral element in the coal, UmHC represents a mass attenuation coefficient of the high-energy gamma ray with regard to the combustible element in the coal, UmHM represents a mass attenuation coefficient of the high-energy gamma ray with regard to the mineral element in the coal, x represents a content of the mineral element in the coal, 1−x represents a content of the combustible element in the coal, and pd represents a mass thickness of the coal, based on $$VL=[y*VmLO+VmLM]*pd/(1+y) \quad (4)$$

$$VH=[y*UmHO+VmHM]*pd/(1+y) \quad (5)$$

$$VmHO \approx VmHM \approx VH \approx UH \quad (6)$$

where VL represents an attenuation coefficient of the second attenuation coefficient of the low-energy gamma ray of the gamma ray with regard to the coal ash, VH represents an attenuation coefficient of the second attenuation coefficient of the high-energy gamma ray of the gamma ray with regard to the coal ash, VmLO represents a mass attenuation coefficient of the low-energy gamma ray with regard to an oxygen element in the coal ash, VmLM represents a mass attenuation coefficient of the low-energy gamma ray with regard to a mineral element in the coal ash, VmHO represents a mass attenuation coefficient of the high-energy gamma ray with regard to the oxygen element in the coal ash, VmHM represents a mass attenuation coefficient of the high-energy gamma ray with regard to the mineral element in the coal ash, and y represents a ratio of a content of the oxygen element in the coal ash to a content of the mineral element in the coal ash, based on $$VmLO \approx UmLC \quad (7)$$

where formula (7) is obtained because a primary combustible in the coal is a carbon element and atomic numbers of the carbon element and the oxygen element are adjacent, and based on $$Ad=x*(1+y)*100 \quad (8)$$

where formula (8) is obtained because the ash content of the coal is equal to a weight percentage of an oxide converted from the mineral element in the coal, the ash content of the coal being obtained according to formula (9)

$$Ad=(UL/UH-C)/(VL/VH-C)*100 \quad (9)$$

where C=UmLC/UH, and C is approximately a constant determined by a theoretical computation or an in-site contrast experiment.

In one embodiment of the present disclosure, in practice, the formula (9) for computing the ash content of the coal is modified as:

$$Ad = A1*(UL/UH)/(VL/VH-C1) - B1/(VL/VH-C1) - D1 \qquad (10)$$

where A1, B1 and D1 are constants determined by an in-site contrast experiment, and C1 is a constant equal to C or a constant determined by an in-site contrast experiment.

In one embodiment of the present disclosure, in practice, the formula (9) for computing the ash content of the coal is modified as:

$$Ad = A2*(UL/UH-C2)/(VL/VH-C2) + B2 \qquad (11)$$

where A2, B2 and C2 are constants determined by an in-site contrast experiment.

With the system and the method for measuring the ash content and the calorific value of the coal according to embodiments of the present disclosure, by disposing the dual-energy gamma ray transmission measuring devices before the inlet of the coal combustion apparatus and after the outlet of the coal combustion apparatus respectively, an attenuation coefficient of a gamma ray from the dual-energy gamma ray transmission measuring device disposed before the inlet of the coal combustion apparatus with regard to the coal (i.e., the first attenuation coefficient) and an attenuation coefficient of a gamma ray the dual-energy gamma ray transmission measuring device disposed after the outlet of the coal combustion apparatus with regard to the coal ash (i.e., the second attenuation coefficient) are measured respectively, and the ash content and the calorific value of the coal are thus computed according to the first attenuation coefficient and the second attenuation coefficient. Therefore, not only may requirements of real-time measurement be met, but also an influence of a change in a content of a high-atomic-number element in the coal on a measurement of the ash content and the calorific value of the coal may be eliminated, thus enabling the measurement to be more accurate and not to be influenced by the change in a coaly.

The above summary of the present disclosure is not intended to describe each disclosed embodiment or every implementation of the present disclosure. The Figures and the detailed description which follow more particularly exemplify illustrative embodiments.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference to the accompanying drawings, in which.

DETAILED DESCRIPTION

Figure 1:
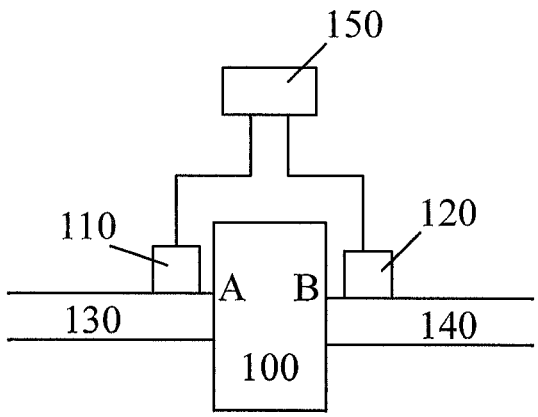
FIG. 1 is a schematic view of a system for measuring an ash content and a calorific value of a coal according to an embodiment of the present disclosure.

Reference will be made in detail to embodiments of the present disclosure. The embodiments described herein with reference to drawings are explanatory, illustrative, and used to generally understand the present disclosure. The embodiments shall not be construed to limit the present disclosure. The same or similar elements and the elements having same or similar functions are denoted by like reference numerals throughout the descriptions.

Various embodiments and examples are provided in the following description to implement different structures of the present disclosure. In order to simplify the present disclosure, certain elements and settings will be described. However, these elements and settings are only examples and are not intended to limit the present disclosure. In addition, reference numerals may be repeated in different examples in the disclosure. This repeating is for the purpose of simplification and clarity and does not refer to relations between different embodiments and/or settings. Furthermore, examples of different processes and materials are provided in the present disclosure. However, it would be appreciated by those skilled in the art that other processes and/or materials may be also applied. Moreover, a structure in which a first feature is "on" a second feature may include an embodiment in which the first feature directly contacts the second feature and may include an embodiment in which an additional feature is prepared between the first feature and the second feature so that the first feature does not directly contact the second feature.

In addition, terms such as "first" and "second" are used herein for purposes of description and are not intended to indicate or imply relative importance or significance. Therefore, a "first" or "second" feature may explicitly or implicitly comprise one or more features. Further, in the description, unless indicated otherwise, "a plurality of" refers to two or more.

FIG. 1 is a schematic view of a system for measuring an ash content and a calorific value of a coal according to an embodiment of the present disclosure. As shown in FIG. 1, the system comprises two dual-energy gamma ray transmission measuring devices 110 and 120 and a computing device 150. The dual-energy gamma ray transmission measuring device 110 is disposed before an inlet A of a coal combustion apparatus 100 for measuring a first attenuation coefficient of a gamma ray from the dual-energy gamma ray transmission measuring device 110 with regard to the coal before combusted. The dual-energy gamma ray transmission measuring device 120 is disposed after an outlet B of the coal combustion apparatus 100 for measuring a second attenuation coefficient of a gamma ray from the dual-energy gamma ray transmission measuring device 120 with regard to a coal ash formed by combusting the coal. The two dual-energy gamma ray transmission measuring devices 110 and 120 are connected with the computing device 150 respectively to transmit the first attenuation coefficient and the second attenuation coefficient to the computing device 150. The computing device 150 is configured to compute the ash content and/or the calorific value of the coal based on the first attenuation coefficient and the second attenuation coefficient. Specifically, the two dual-energy gamma ray transmission measuring devices 110 and 120 are connected with the computing device 150 respectively via a cable or a wireless communication.

It should be pointed out that since the dual-energy gamma ray transmission measuring device containing two types of dual-energy gamma rays with different levels of energy is well known to those skilled in the art, a structure and a function of the dual-energy gamma ray transmission measuring device will not be described in detail herein. In addition, the system with two dual-energy gamma ray transmission measuring devices is taken as an example in this embodiment, however, in practice, there may be a plurality of transmission bands configured to supply the coal to the coal combustion apparatus, and thus each transmission band needs to be equipped with one dual-energy gamma ray transmission measuring device, that is, a plurality of dual-energy gamma ray transmission measuring devices are disposed before the inlet A of the coal combustion apparatus 100.

In one embodiment, the coal combustion apparatus 100 may be a boiler. A coal transmission band 130 is connected to the inlet A of the boiler 100 for inputting the coal to be combusted to the boiler 100. A coal ash transmission band 140 is connected to the outlet B of the boiler 100 for outputting the coal to be combusted from the boiler 100. Preferably, the dual-energy gamma ray transmission measuring device 110 is disposed above the coal transmission band 130, and the dual-energy gamma ray transmission measuring device 120 is disposed above the coal ash transmission band 140.

In one embodiment, a coal ash sampling apparatus may be disposed near the outlet B of the coal combustion apparatus 100 for sampling the coal ash formed by combusting the coal. In particular, the dual-energy gamma ray transmission measuring device 120 may be disposed above the coal ash sampling apparatus for measuring the second attenuation coefficient.

In one embodiment, a correction delay time of the system is set based on a system running time for which the coal is transmitted from a first position where the first attenuation coefficient is measured to a second position where the second attenuation coefficient is measured, and the ash content and the calorific value of the coal are computed by the computing device 150 based on the second attenuation coefficient measured at a current time and the first attenuation coefficient measured at a time which is one correction delay time forward from the current time. By setting the correction delay time of the system, it is ensured that the first attenuation coefficient and the second attenuation coefficient are measured for the same coal. Because a part of the first attenuation coefficient influenced by the change in a content of a high-atomic-number element is deducted by using the second attenuation coefficient, the ash content and/or the calorific value of the coal may be computed accurately.

In one embodiment, the ash content and the calorific value of the coal are computed by the computing device 150 based on the first attenuation coefficient measured at the current time and an average of a plurality of second attenuation coefficients measured in a fixed period of time forward from the current time. The fixed period of time may be determined and adjusted according to various applications.

Figure 2:
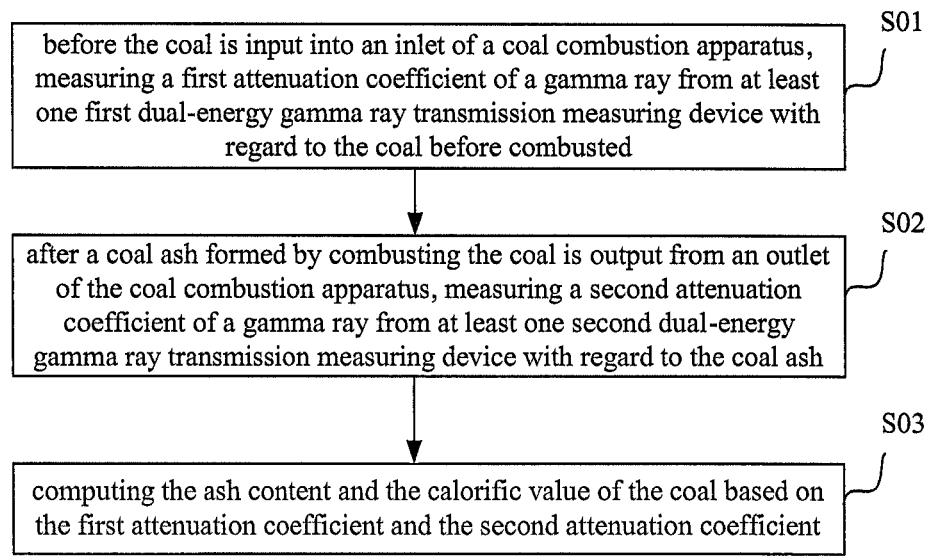
FIG. 2 is a flow chart of a method for measuring the ash content and the calorific value of the coal according to an embodiment of the present disclosure.

A method for measuring an ash content and a calorific value of a coal is further provided according to an embodiment of the present disclosure. As shown in FIG. 2, the method comprises following steps.

Step S01, before the coal is input into the inlet A of the coal combustion apparatus 100, a first attenuation coefficient of a gamma ray from at least one first dual-energy gamma ray transmission measuring device (such as the dual-energy gamma ray transmission measuring device 110) with regard to the coal before combusted is measured.

Step S02, after the coal ash formed by combusting the coal is output from the outlet B of the coal combustion apparatus 100, a second attenuation coefficient of a gamma ray from at least one second dual-energy gamma ray transmission measuring device (such as the dual-energy gamma ray transmission measuring device 120) with regard to the coal ash is measured.

Step S03, the ash content and the calorific value of the coal are computed based on the first attenuation coefficient and the second attenuation coefficient. In one embodiment, a computing method may be illustrated in detail as follows.

Based on $$UL=[(1-x)*UmLC+x*UmLM]*pd \quad (1)$$

$$UH=[(1-x)*UmHC+x*UmHM]*pd \quad (2)$$

$$UmHC \approx UmHM \approx UH \quad (3)$$

where UL represents an attenuation coefficient of the first attenuation coefficient of a low-energy gamma ray of the gamma ray with regard to the coal, UH represents an attenuation coefficient of the first attenuation coefficient of a high-energy gamma ray of the gamma ray with regard to the coal, UmLC represents a mass attenuation coefficient of the low-energy gamma ray with regard to a combustible element in the coal, UmLM represents a mass attenuation coefficient of the low-energy gamma ray with regard to a mineral element in the coal, UmHC represents a mass attenuation coefficient of the high-energy gamma ray with regard to the combustible element in the coal, UmHM represents a mass attenuation coefficient of the high-energy gamma ray with regard to the mineral element in the coal, x represents a content of the mineral element in the coal, 1−x represents a content of the combustible element in the coal, and pd represents a mass thickness of the coal, based on $$VL=[y*VmLO+VmLM]*pd/(1+y) \quad (4)$$

$$VH=[y*UmHO+VmHM]*pd/(1+y) \quad (5)$$

$$VmHO \approx VmHM \approx VH \approx UH \quad (6)$$

where VL represents an attenuation coefficient of the second attenuation coefficient of the low-energy gamma ray of the gamma ray with regard to the coal ash, VH represents an attenuation coefficient of the second attenuation coefficient of the high-energy gamma ray of the gamma ray with regard to the coal ash, VmLO represents a mass attenuation coefficient of the low-energy gamma ray with regard to an oxygen element in the coal ash, VmLM represents a mass attenuation coefficient of the low-energy gamma ray with regard to a mineral element in the coal ash, VmHO represents a mass attenuation coefficient of the high-energy gamma ray with regard to the oxygen element in the coal ash, VmHM represents a mass attenuation coefficient of the high-energy gamma ray with regard to the mineral element in the coal ash, and y represents a ratio of a content of the oxygen element in the coal ash to a content of the mineral element in the coal ash, based on $$VmLO \approx UmLC \quad (7)$$

where formula (7) is obtained because a primary combustible in the coal is a carbon element and atomic numbers of the carbon element and the oxygen element are adjacent, and based on $$Ad=x*(1+y)*100 \quad (8)$$

where formula (8) is obtained because the ash content of the coal is equal to a weight percentage of an oxide converted from the mineral element in the coal, the ash content of the coal is obtained according to formula (9)

$$Ad=(UL/UH-C)/(VL/VH-C)*100 \quad (9)$$

where $C=UmLC/UH$, and C is approximately a constant determined by a theoretical computation or an in-site contrast experiment.

Because there is an approximation in the above derivation process and a physical model, in order to optimize a measuring result, in practice, the formula (9) for computing the ash content of the coal may be modified by adding a coefficient.

In one embodiment, a modified formula (10) for computing the ash content of the coal may be as follows:

$$Ad = A1*(UL/UH)/(VL/VH-C1)-B1/(VL/VH-C1)-D1 \quad (10)$$

where A1, B1 and D1 are constants determined by an in-site contrast experiment, and C1 is a constant equal to C or a constant determined by an in-site contrast experiment.

In another embodiment, a modified formula (11) for computing the ash content of the coal may be as follows:

$$Ad = A2*(UL/UH-C2)/(VL/VH-C2)+B2 \quad (11)$$

where A2, B2 and C2 are constants determined by an in-site contrast experiment.

It should be noted that, the modified formulas listed above are exemplary, which shall not be construed to limit the present disclosure. According to a practical application, by using the above ash content modification principle and method, a formula in a different form derived by those skilled in the art shall also be included in the scope of the present disclosure.

It can be known from the above formulas for computing the ash content of the coal that, the coal ash, with regard to which the second attenuation coefficient is measured, in theory shall be generated by the coal, with regard to which the first attenuation coefficient is measured, so that the ash content and the calorific value of the coal may be accurately computed based on the first attenuation coefficient and the second attenuation coefficient. Because there is a system running time from a time when the coal is input into the coal combustion apparatus to a time when the coal ash is generated and output after the coal is combusted, the system running time shall be taken into account if a strict computation of the ash content is conducted. In one embodiment of the present disclosure, a correction delay time is set based on the system running time for which the coal is transmitted from a first position where the first attenuation coefficient is measured to a second position where the second attenuation coefficient is measured, and the ash content and the calorific value of the coal are computed based on the second attenuation coefficient measured at a current time and the first attenuation coefficient measured at a time which is one correction delay time forward from the current time. By setting the correction delay time of the system, it is ensured that the first attenuation coefficient and the second attenuation coefficient are measured for the same coal. Because a part of the first attenuation coefficient influenced by the change in the content of the high-atomic-number element is deducted by using the second attenuation coefficient, the ash content and/or the calorific value of the coal may be computed accurately. Although the ash content and the calorific value of the coal computed in this way will delay for a period of time, they still play a guiding role in production and have a significance for analysing an energy conservation efficiency.

Alternatively, there is another solution to correct the measuring result. In this solution, the ash content and the calorific value of the coal are computed based on the first attenuation coefficient measured at the current time and an average of a plurality of second attenuation coefficients measured in a fixed period of time (for example, 10-30 minutes) forward from the current time, and thus a better measuring result may be obtained. The fixed period of time may be adjusted according to various applications. Because a probability of a larger change in the coaly is slight within a short time interval, the average of the plurality of second attenuation coefficients may represent an actual second attenuation coefficient within a future short time. Furthermore, an error of the second attenuation coefficient by averaging is smaller, which is favorable for the measurement.

With the system and the method for measuring the ash content and the calorific value of the coal according to embodiments of the present disclosure, by disposing the dual-energy gamma ray transmission measuring devices before the inlet of the coal combustion apparatus and after the outlet of the coal combustion apparatus respectively, an attenuation coefficient of a gamma ray from the dual-energy gamma ray transmission measuring device disposed before the inlet of the coal combustion apparatus with regard to the coal (i.e., the first attenuation coefficient) and an attenuation coefficient of a gamma ray the dual-energy gamma ray transmission measuring device disposed after the outlet of the coal combustion apparatus with regard to the coal ash (i.e., the second attenuation coefficient) are measured respectively, and the ash content and the calorific value of the coal are thus computed according to the first attenuation coefficient and the second attenuation coefficient. Therefore, not only may requirements of real-time measurement be met, but also an influence of a change in a content of a high-atomic-number element in the coal on a measurement of the ash content and the calorific value of the coal may be eliminated, thus enabling the measurement to be more accurate and not to be influenced by the change in a coaly.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments can not be construed to limit the present disclosure, and changes, alternatives, and modifications can be made in the embodiments without departing from spirit, principles and scope of the present disclosure.

What is claimed is:

1. A system for measuring an ash content and a calorific value of a coal, comprising:
   at least two dual-energy gamma ray transmission measuring devices and a computing device, wherein
   at least one first dual-energy gamma ray transmission measuring device is disposed before an inlet of a coal combustion apparatus for measuring a first attenuation coefficient of a gamma ray from the at least one first dual-energy gamma ray transmission measuring device with regard to the coal before combusted;
   at least one second dual-energy gamma ray transmission measuring device is disposed after an outlet of the coal combustion apparatus for measuring a second attenuation coefficient of a gamma ray from the at least one second dual-energy gamma ray transmission measuring device with regard to a coal ash formed by combusting the coal; and the at least two dual-energy gamma ray transmission measuring devices are connected with the computing device respectively to transmit the first attenuation coefficient and the second attenuation coefficient to the computing device, and the computing device is configured to compute the ash content and the calorific value of the coal based on the first attenuation coefficient and the second attenuation coefficient.

2. The system of claim 1, wherein the at least two dual-energy gamma ray transmission measuring devices are connected with the computing device respectively via a cable or a wireless communication.

3. The system of claim 1, wherein the at least one first dual-energy gamma ray transmission measuring device is disposed on a first transmission band connected with the inlet of the coal combustion apparatus.

4. The system of claim 1, wherein the at least one second dual-energy gamma ray transmission measuring device is disposed above a second transmission band connected with the outlet of the coal combustion apparatus.

5. The system of claim 1, wherein the at least one second dual-energy gamma ray transmission measuring device is disposed on a coal ash sampling apparatus near the outlet of the coal combustion apparatus for measuring the second attenuation coefficient of the coal ash output by the coal combustion apparatus and sampled by the coal ash sampling apparatus.

6. The system of claim 1, wherein a correction delay time of the system is set based on a system running time for which the coal is transmitted from a first position where the first attenuation coefficient is measured to a second position where the second attenuation coefficient is measured, and the ash content and the calorific value of the coal are computed by the computing device based on the second attenuation coefficient measured at a current time and the first attenuation coefficient measured at a time which is one correction delay time forward from the current time.

7. The system of claim 1, wherein the ash content and the calorific value of the coal are computed by the computing device based on the first attenuation coefficient measured at a current time and an average of a plurality of second attenuation coefficients measured in a fixed period of time forward from the current time.

8. A method for measuring an ash content and a calorific value of a coal, comprising steps of:

S01: before the coal is input into an inlet of a coal combustion apparatus, measuring a first attenuation coefficient of a gamma ray from at least one first dual-energy gamma ray transmission measuring device with regard to the coal before combusted;

S02: after a coal ash formed by combusting the coal is output from an outlet of the coal combustion apparatus, measuring a second attenuation coefficient of a gamma ray from at least one second dual-energy gamma ray transmission measuring device with regard to the coal ash;

S03: computing the ash content and the calorific value of the coal based on the first attenuation coefficient and the second attenuation coefficient.

9. The method of claim 8, wherein a correction delay time is set based on a system running time for which the coal is transmitted from a first position where the first attenuation coefficient is measured to a second position where the second attenuation coefficient is measured, and the ash content and the calorific value of the coal are computed based on the second attenuation coefficient measured at a current time and the first attenuation coefficient measured at a time which is one correction delay time forward from the current time.

10. The method of claim 8, wherein the ash content and the calorific value of the coal are computed based on the first attenuation coefficient measured at a current time and an average of a plurality of second attenuation coefficients measured in a fixed period of time forward from the current time.

11. The method of claim 8, wherein step S03 comprises steps of:

based on $$UL=[(1-x)*UmLC+x*UmLM]*pd \quad (1)$$

$$UH=[(1-x)*UmHC+x*UmHM]*pd \quad (2)$$

$$UmHC \approx UmHM \approx UH \quad (3)$$

where UL represents an attenuation coefficient of the first attenuation coefficient of a low-energy gamma ray of the gamma ray with regard to the coal, UH represents an attenuation coefficient of the first attenuation coefficient of a high-energy gamma ray of the gamma ray with regard to the coal, UmLC represents a mass attenuation coefficient of the low-energy gamma ray with regard to a combustible element in the coal, UmLM represents a mass attenuation coefficient of the low-energy gamma ray with regard to a mineral element in the coal, UmHC represents a mass attenuation coefficient of the high-energy gamma ray with regard to the combustible element in the coal, UmHM represents a mass attenuation coefficient of the high-energy gamma ray with regard to the mineral element in the coal, x represents a content of the mineral element in the coal, 1−x represents a content of the combustible element in the coal, and pd represents a mass thickness of the coal, based on $$VL=[y*VmLO+VmLM]*pd/(1+y) \quad (4)$$

$$VH=[y*UmHO+VmHM]*pd/(1+y) \quad (5)$$

$$VmHO \approx VmHM \approx VH \approx UH \quad (6)$$

where VL represents an attenuation coefficient of the second attenuation coefficient of the low-energy gamma ray of the gamma ray with regard to the coal ash, VH represents an attenuation coefficient of the second attenuation coefficient of the high-energy gamma ray of the gamma ray with regard to the coal ash, VmLO represents a mass attenuation coefficient of the low-energy gamma ray with regard to an oxygen element in the coal ash, VmLM represents a mass attenuation coefficient of the low-energy gamma ray with regard to a mineral element in the coal ash, VmHO represents a mass attenuation coefficient of the high-energy gamma ray with regard to the oxygen element in the coal ash, VmHM represents a mass attenuation coefficient of the high-energy gamma ray with regard to the mineral element in the coal ash, and y represents a ratio of a content of the oxygen element in the coal ash to a content of the mineral element in the coal ash, based on $$VmLO \approx UmLC \quad (7)$$

where formula (7) is obtained because a primary combustible in the coal is a carbon element and atomic numbers of the carbon element and the oxygen element are adjacent, and based on $$Ad = x*(1+y)*100 \qquad (8)$$

where formula (8) is obtained because the ash content of the coal is equal to a weight percentage of an oxide converted from the mineral element in the coal, the ash content of the coal being obtained according to formula (9)

$$Ad = (UL/UH-C)/(VL/VH-C)*100 \qquad (9)$$

where C=UmLC/UH, and C is approximately a constant determined by a theoretical computation or an in-site contrast experiment.

12. The method of claim 11, wherein in practice, the formula (9) for computing the ash content of the coal is modified as:

$$Ad = A1*(UL/UH)/(VL/VH-C1)-B1/(VL/VH-C1)-D1 \qquad (10)$$

where A1, B1 and D1 are constants determined by an in-site contrast experiment, and C1 is a constant equal to C or a constant determined by an in-site contrast experiment.

13. The method of claim 11, wherein in practice, the formula (9) for computing the ash content of the coal is modified as:

$$Ad = A2*(UL/UH-C2)/(VL/VH-C2)+B2 \qquad (11)$$

where A2, B2 and C2 are constants determined by an in-site contrast experiment.

* * * * *